KALANCHOE PLANT
Filed May 13, 1974 2 Sheets-Sheet 1
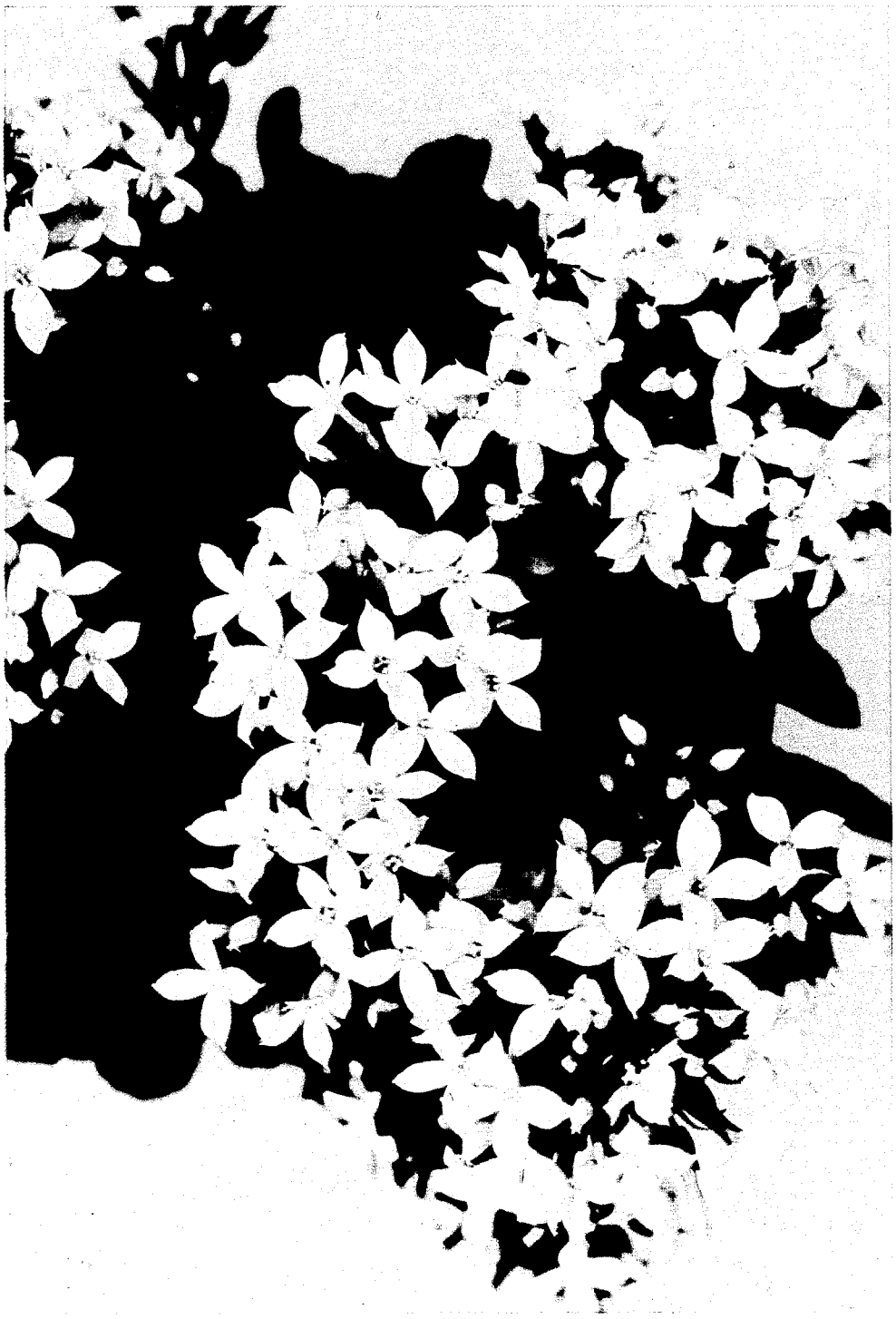

KALANCHOE PLANT
Filed May 13, 1974 2 Sheets-Sheet 2
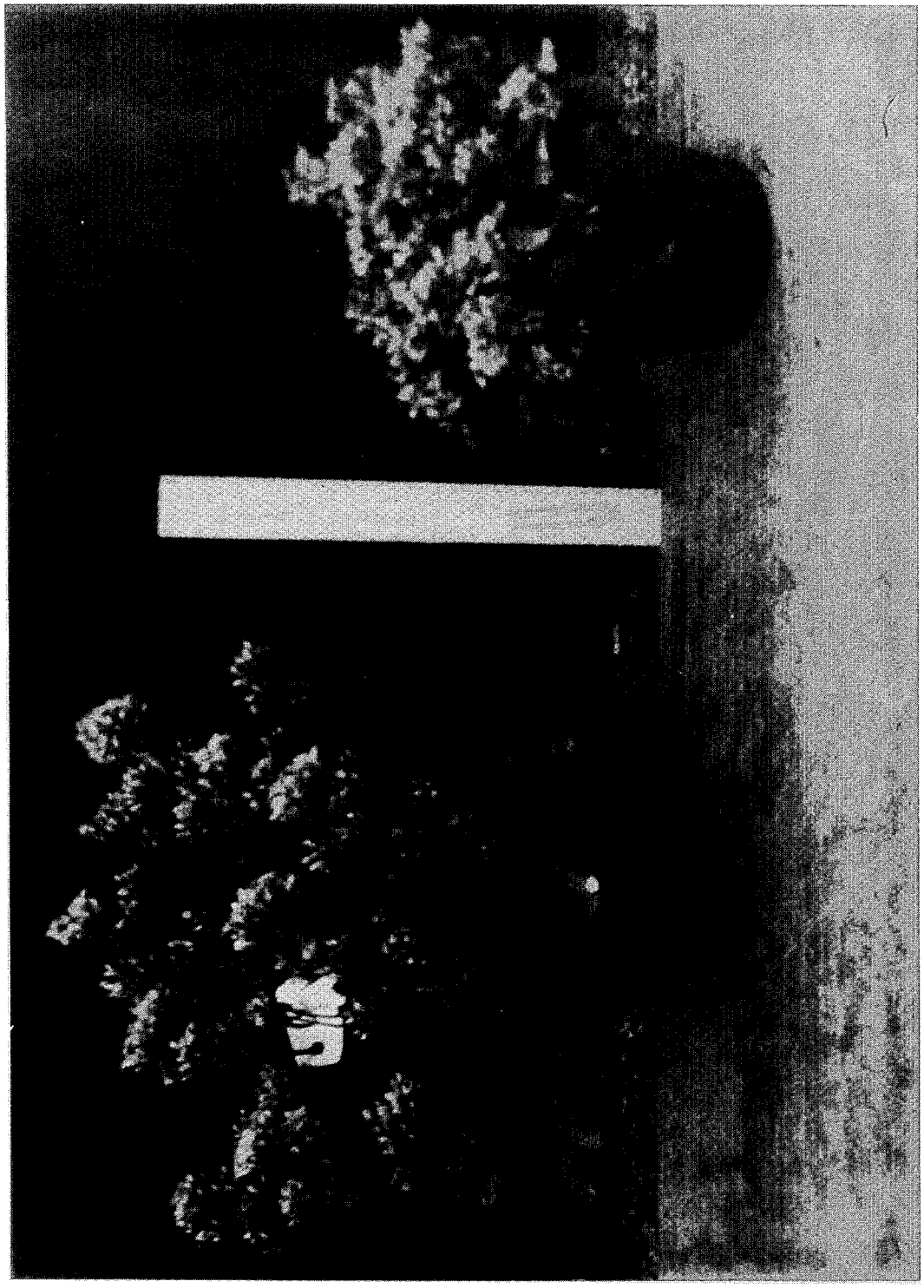

United States Patent

Plant Pat. 3,765

Patented Aug. 19, 1975

3,765

KALANCHOE PLANT

Lawrence T. Irwin, Amarillo, Tex., assignor to J and L Plants, Incorporated, Canyon, Tex.

Filed May 13, 1974, Ser. No. 469,699

Int. Cl. A01h 5/00

U.S. Cl. Pl.—68 1 Claim

The present invention relates to a new and distinct variety of kalanchoe plant which was discovered by me as a cultivated sport of the kalanchoe variety known as "Exotic Gold" (Plant Pat. No. 3,285), said discovery having been made by me in a large block of "Exotic Gold" plants being grown in greenhouses located in Canyon, Tex., under my direction and supervision.

At the time of my discovery, my attention was attracted to one particular plant in the block aforesaid which appeared to be extremely dwarf in size and which was bearing blooms much earlier than the normal blooming date of the other plants of the block. Close inspection of that plant indicated that it was apparently a sport mutation of "Exotic Gold," so I carefully preserved the sport and continued to keep it under close observation. In due course, I asexually reproduced the sport by cuttings, as performed by me in the greenhouses aforementioned at Canyon, Tex. My continued observations of the original sport and the progeny thereof derived from the asexual propagations aforesaid, confirmed its distinctiveness, and fully convinced me that it was a new and improved kalanchoe variety, as evidenced by the following unique combination of principal characteristics which are outstanding therein:

(1) An extremely dwarf habit of growth as compared with the normal growth habit of its parent "Exotic Gold" and other kalanchoe varieties;
(2) A much more self-branching habit;
(3) An earlier blooming habit ranging from about 7 to 10 days earlier than "Exotic Gold"; and
(4) A foliage and flower color basically similar to those of "Exotic Gold."

The accompanying drawings show a typical blooming plant specimen of my new variety as depicted in color as nearly true as it is reasonably possible to make the same in a color illustration of this character, as well as a comparative view in black and white, depicting the comparative heights of the new dwarf variety and the much taller parent variety.

The following is a detailed description of my new kalanchoe variety, with color terminology in accordance with The Exotica Horticultural Color Guide, published by Roehrs Company, except where general color terms of ordinary dictionary significance are obvious:

PARENTAGE: Sport of "Exotic Gold."

PROPAGATION: Holds its distinguishing characteristics through succeeding propagations by direct rooting of cuttings.

LOCALITY WHERE GROWN AND OBSERVED: Canyon, Tex.

PLANT:

Form—Dwarf (from about 7 inches to 9 inches tall which is about half the normal height of the parent variety which usually attains a height of about 20 inches more or less when grown under the same conditions); much-branched; compact.

Growth habit—Dwarf; branching; compact.

Rooting habit—Roots easily from from any part of stem, forming a fibrous root system.

Blooming habit—Flowers naturally about Dec. 1.

Blooming season—Can be brought into bloom the year around by appropriate photo-periodic manipulation.

FOLIAGE:

Size—Small; about 2¾ inches long (including petiole); about 2 inches wide.

Quantity—Normal.

Color—New foliage—Upper side—Fern Green, No. 83; under side—Fern Green, No. 83—. Old foliage—Upper side—Fern Green, No. 83+; under side—Fern Green, No. 83—.

Texture—Upper side—Glossy; smooth. Under side—smooth.

Margin—Irregularly crenate.

Shape—Basically elliptical, with obtuse tip and obtuse to acute base of leaf.

DISEASE RESISTANCE: Comparable to that of "Exotic Gold" which is much more resistant to soil diseases than old standard kalanchoe varieties, as determined by comparison with other varieties grown under the same greenhouse conditions at Canyon, Tex.

FLOWER: Complete.

Diameter—About 23/32 inch.

Depth—About 9/16 inch.

Petal length—About 19/64 inch.

Petal width—About 5/32 inch.

Form—Compound umbel; section petals united; ovary superior.

Color of petals—Upper side—Graduates from Apricot, No. 11 at tip to Chrome Yellow, No. 1 at base of petal. Under side—Peach Pink, No. 15.

Blooming period—From about 3 to 5 weeks.

FRUIT: None.

HARDINESS: Good throughout range of about 50° F. to 100° F.

GENERAL OBSERVATIONS: The new variety has all the qualities necessary for an excellent small unit potted plant for mass market sales, and its extreme dwarfness, self-branching and early blooming habit is unique for the species.

I claim:

1. A new and distinct variety of kalanchoe plant, substantially as herein shown and described, characterized particularly as to novelty by the unique combination of an extremely dwarf habit of growth as compared with the normal growth habit of its parent "Exotic Gold" and other kalanchoe varieties; a much more self-branching habit; an earlier blooming habit ranging from about 7 to 10 days earlier than "Exotic Gold"; and a foliage and flower color basically similar to those of "Exotic Gold."

No references cited.

ROBERT E. BAGWILL, Primary Examiner